US000001406H

United States Statutory Invention Registration [19]

[11] Reg. Number: H1406

Powers

[43] Published: Jan. 3, 1995

[54] PROCESS FOR PREPARING DIBENZOFURANS VIA CATALYTIC HETEROANNULATION

[75] Inventor: Matthew R. Powers, Barto, Pa.

[73] Assignee: Rhône Poulenc Rorer Pharmaceuticals Inc., Collegeville, Pa.

[21] Appl. No.: 54,982

[22] Filed: Apr. 30, 1993

[51] Int. Cl.[6] ..... C07D 307/91

[52] U.S. Cl. ..... 549/461

[58] Field of Search ..... 549/461

[56] References Cited

U.S. PATENT DOCUMENTS 4,863,921 9/1989 Youssefyeh et al. ..... 514/230.5

OTHER PUBLICATIONS

Busch et al '1,2,3,4,4a,9b-hexahydro-4-hydroxydibenzofurans' CA 96:19951q (1982).

Toth et al 'Total synthesis of dl morphine' J. Org Chem. vol. 52, No. 3 pp. 473-475 (1987).

Matharu et al 'Synthesis and antitussive activity . . . ' J. Med. Chem vol. 20, No. 2 pp. 197-204 (1977).

Youssefyeh et al 'Development of high-affinity . . . ' J. Med Chem vol. 35, No. 5 pp. 895-903 (1992).

Youssefyeh et al 'Development of high-affinity 5-HT3 Receptor Antagonists.' J. Med. Chem vol. 35, No. 5 pp. 903-911 (1992).

Skaletzky 'Cycloalka[b]benzofuranols' CA 68:21826t (1968).

Busch et al '1,2,3,4,4a,9b-hexahydro-4-aminodibenzofurans' CA 96:142689n (1982).

*Primary Examiner*—Shean Wu

*Attorney, Agent, or Firm*—James A. Nicholson; Martin F. Savitzky; Raymond S. Parker, III

[57] ABSTRACT

The present invention is directed to the synthesis of 2-chloro-cis-[5a(S)-9a(S)-(5a,6,7,8,9,9a-hexahydro)]-dibenzofuran-4-carboxylic acid by a stereospecific catalytic heteroannulation synthesis free of undesirable 8-chloro-2,6-methano-2H-3,4,5,6-tetrahydro-1-benzoxocin-10-carboxylic.

1 Claim, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR PREPARING DIBENZOFURANS VIA CATALYTIC HETEROANNULATION

BACKGROUND OF THE INVENTION

The tetra and hexahydrodibenzofuran ring systems are common in biologically active natural compounds (Toth, J. E., et al. J. Org. Chem. 1987, 52, 473). Analogs containing these structural features have been studied for a variety of indications, such as: antipsychotics (Busch, N., et al. French Patent 2 482 966, 1981), analgesics (Skaletzky, L. L. U.S. Pat. No. 3,317,527, 1967), antitussives (Matharu, S. S., et al. J. Med. Chem. 1977, 20, 197), CNS stimulants (Skaletzky, L. L. U.S. Pat. No. 3,317,527, 1967), and antiemetics (Youssefyeh, R. D., et al. J. Med. Chem. 1992, 35, 895).

Methods for obtaining these ring systems therefore are of considerable interest. Among the reported compounds which have valuable antiemetic and antipsychotic properties is 4-[N-(1-azabicyclo[2.2.2]octan-3-yl)]-2-chloro-[5a,6,7,8,9,9a-hexahydro]dibenzofurancarboxamide. This racemic compound has eight possible stereoisomers, and it has been reported that 4-[N-(1-azabicyclo-[2.2.2]octan-3(S)-yl)]-2-chloro-[5a(S)-9a(S)-(5a,6,7,8,9,9a-hexahydro)]dibenzofurancarboxamide is the most active of the isomers. This is shown as Formula I.

Formula I

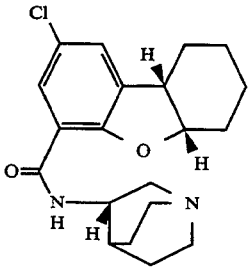

The compound of Formula I is prepared by the reaction of 2-chloro-5a,6,7,8,9,9a-hexahydrodibenzofuran-4-carboxylic acid with 3-aminoquinuclidine and is described in U.S. Pat. No. 4,863,921.

REPORTED DEVELOPMENTS

Of interest is the synthesis of both enantiomers but the synthesis of the S,S enantiomer of 2-chloro-cis-(5a,6,7,8,9,9a-hexahydro)]dibenzofuran-4-carboxylic acid is particularly interesting. Synthesis of these isomers has been reported using semipreparative chiral HPLC and classical resolution (Youssefyeh, R. D.; et al J. Med. Chem. 1992, 35, 903).

The above reported synthesis is described by the following Scheme I.

Scheme I

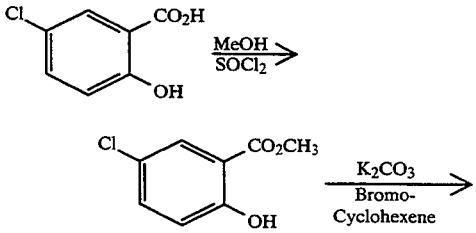

-continued

Scheme I

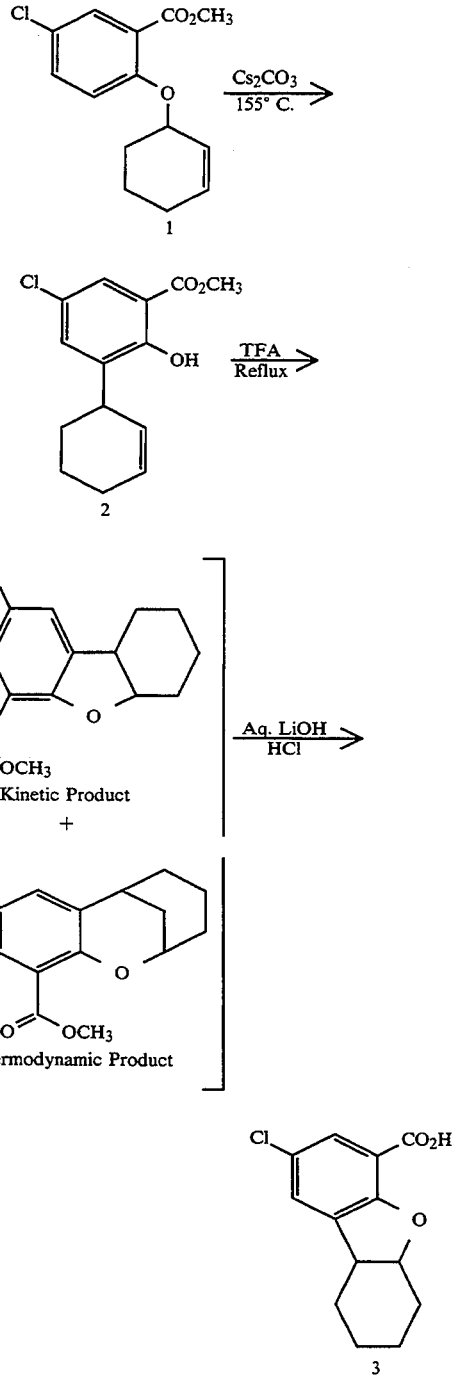

This starts with an alkylation of methyl 5-chlorosalicylate with 3-bromocyclohexene to afford methyl 5-chloro-2-(3'-cyclohexenyl)salicylate (1). After a thermal Claisen rearrangement is performed to afford methyl 5-chloro-3-(3'-cyclohexenyl)salicylate (2) an intramolecular cyclization with trifluroacetic acid followed by hydrolysis yields racemic 2-chloro-cis-(5a,6,7,8,9,9a-hexahydro]-dibenzofurancarboxylic acid and also results in the formation of a thermo-dynamically favored product, 8-chloro-2,6-methano-2H-3,4,5,6-tetrahydro- 1-benzoxocin-10-carboxylic acid. The chiral acids are then obtained by fractional recrystallization as the R or S α-methylbenzylamine salt. This is a 7 step synthesis.

A second procedure for obtaining 2-chloro-cis-[5a(S)-9a(S)-(5a,6,7,8,9,9a-hexahydro)]dibenzofuran-4-carboxylic acid is by the transfer of chirality in a Claisen rearrangements. This is described in the following Scheme II.

Scheme II

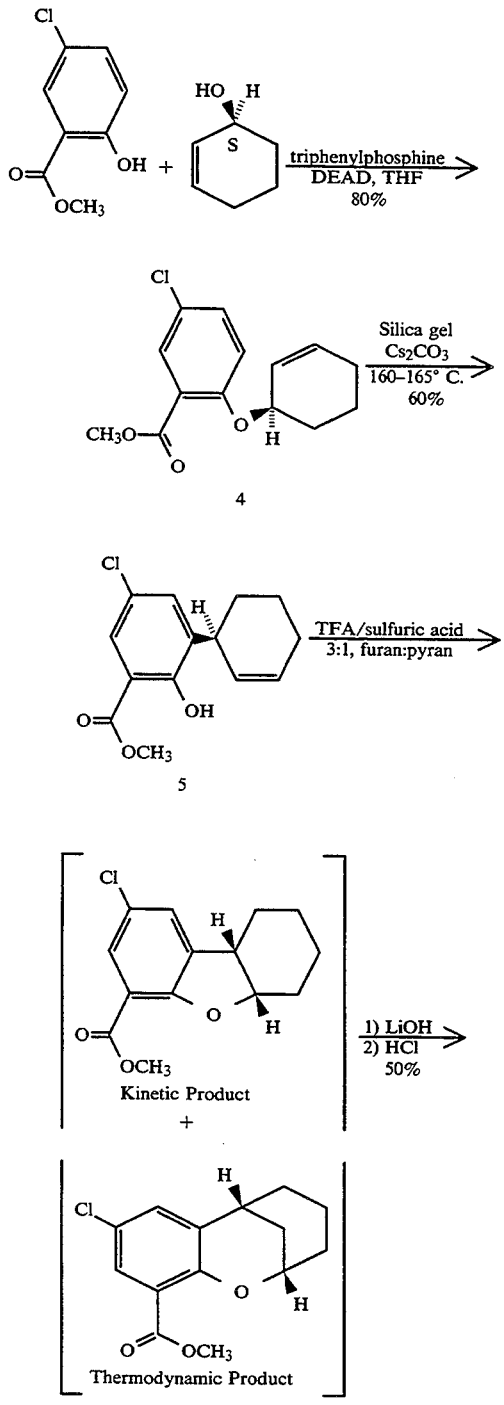

-continued

Scheme II

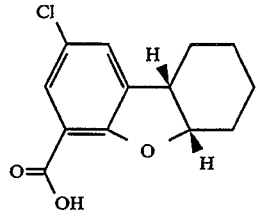

3 S,S

This is a more direct approach to obtain a stereospecific synthesis and describes the Claisen rearrangement with a chiral ether (4). S-2-Cyclohexene-1-ol was obtained by asymmetric ring opening of cyclohexene oxide. A Mitsunobu condensation between S-cyclohexanol and methyl 5-chlorosalicylate provided the chiral ether 4. The thermal Claisen rearrangement of 4 afforded 5 in moderate yield along with the products of elimination, cyclohexadiene and methyl 5-chloro-salicylate. Acid catalyzed intramolecular cyclization yielded a 3 to 1 mixture of structural isomers shown in Scheme II. The benzofuran isomer is the kinetic product and can be converted to the thermodynamically favored benzoxocin isomer by treatment with concentrated sulfuric acid as reported earlier (R. D. Youssefyeh et al. J. Med. Chem. 1992, 35, 903). Upon hydrolysis with lithium hydroxide the benzofuran isomer precipitates out as the lithium salt and is easily separated by filtration. Acidification of this material yields 2-chloro-[5a(S)-9a(S)-(5a,6,7,8,9,9a-hexahydro)]dibenzofuran-4-carboxylic acid (3 S,S) in 5 steps, which is similar to the material obtained by classical resolution, the structural determination of which was made by X-ray crystallography. The Claisen rearrangement using S-cyclohexanol proceeds in only moderate yield, and one quarter to one third of the chiral material obtained is lost as the benzopyran isomer.

The present invention is directed to the synthesis of 2-chloro-cis-[5a(S)-9a(S)-(5a, 6,7,8,9,9a-hexahydro)]-dibenzofuran-4-carboxylic acid by stereospecific synthesis to obtain the desired isomer.

SUMMARY OF THE INVENTION

We have discovered that the desired 2-chloro-cis-[(5a,6,7,8,9,9a-hexahydro)]dibenzofurancarboxylic acid may be conveniently prepared substantially free of undesirable 8-chloro-2,6-methano-2H-3,4,5,6-tetrahydro-1-benzoxocin-10-carboxylic acid by a catalytic heteroannulation reaction to obtain a cis fused benzofuran system.

DETAILED DESCRIPTION

The catalytic heteroannulation synthesis substantially eliminates the benzoxocine structural isomer and is described by Scheme III below.

Scheme III

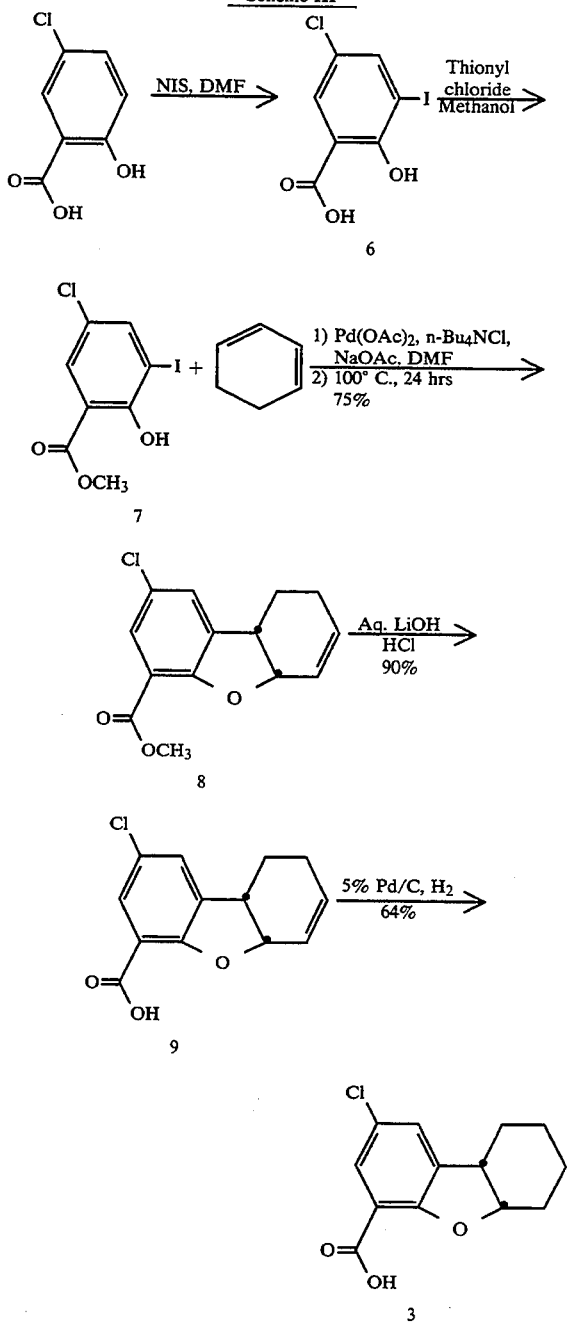

5-Chlorosalicyclic acid is iodinated in the 3 position with N-iodosuccinamide in DMF and esterified with thionyl chloride in methanol to afford 7. Condensation of 7 with cyclohexadiene, and using a catalytic system developed by Larock et al. (Larock, R. C., Berrios-Pena, N., Narayanan, K. J. Org. Chem. 1990, 55, 3447.), methyl 2-chloro-[(5a,8,9,9a-tetrahydro)]-dibenzofuran-carboxylate (8) can be generated in one step with the correct substitution. Lithium hydroxide hydrolysis of 8 followed by reduction with 5% palladium on carbon yields racemic 2-chloro-(5a,6,7,8,9,9a-hexahydro)]-dibenzofurancarboxylic acid 3 in 5 steps from 5-chlorosalicylic acid. This approach provides a simple and direct synthesis of racemic 2-chloro-(5a,6,7,8,9,9a-hexahydro)]dibenzofurancarboxylic acid 3 which may then be resolved without interference from the formation of the benzoxocin isomer.

The following reaction examples describe the process of this invention and are intended to be representative and not to limit the reaction conditions involved.

5-Chloro-3-iodosalicylic Acid (6)

5-Chlorosalicylic acid (20 g, 115.8 mmol) is dissolved in DMF (100 mL). To this solution is added NIS (26.1 g, 116.0 mmol) which causes the reaction to warm up to 60° C. The reaction is stirred at room temperature for 20 hours. At this point ethyl acetate (100 mL) is added and the solution washed with 0.1N HCl (100 mL). The organic phase is then washed with water (3×100 mL), dried with sodium sulfate and evaporated under reduced pressure to yield 5-yield 5-chloro-3-iodosalicylic acid as off-white solid. (mp 160°–163° C.)

Methyl 5-chloro-3-iodosalicylate (7)

Thionyl chloride (30 mL, 411 mmol) is added dropwise to methanol (100 mL) in an ice bath. The addition is controlled to hold the temperature at 25° C. Upon completion of the addition 6 (25 g, 84 mmol) is added and the reaction heated to reflux for 4 hours. The solids dissolve at first then after 2 hours solids start to come out of solution. After 4 hours TLC (hex:EtOAc; 9:1) shows no starting material. The reaction is cooled in the refrigerator for 12h. The solids formed are filtered washed with water (30 mL), and dried under vacuum at 27° C. to yield methyl 5-chloro-3-iodosalicylate as an off white solid. (mp 143°–145° C.)

2-Chloro-cis-5a,8,9,9a-tetrahydrodibenzofuran-4-methylester (8)

A sample of 7 (5 g, 16 mmol) was treated with palladium(II)acetate (0.18 g, 0.8 mmol), tetrabutylammonium chloride (4.5 g, 16 mmol, 1.0 eq), sodium acetate (4.6 g, 56 mmol, 3.5 eq), 1,3-cyclohexadiene (6 g, 82 mmol, 5.0 eq), and DMF (32 mL). The reaction was heated for 24 hours at 100° C., cooled to room temperature, diluted with toluene (30 mL), washed with ammonium chloride (2×60 mL), dried with magnesium sulfate, and the solvent removed under reduced pressure. A yield of 3.3 g (78%) of product was obtained after trituration of the crude material with hexane. (mp. 90°–93° C.)

2-Chloro-cis-5a,8,9,9a-tetrahydrodibenzofuran-4-carboxylic acid (9)

To a slurry of 8 (3 g, 11.4 mmol) in water (60 mL) is added lithium hydroxide monohydrate (0.7 g, 16.2 mmol) and the mixture heated to 65° C. When no more starting material remains by TLC (Hex:EtOAc; 9;1), the mixture is cooled overnight. The precipitated solids are filtered and then slurried in ethyl acetate (45 mL). Deionized water (25 mL) is added to this slurry, which is then acidified with 10% aqueous hydrochloric acid to a pH of 1–2. The layers are separated and the ethyl acetate phase concentrated to dryness to give 2-chloro-cis-5a,8,9,9a-tetrahydrodibenzofuran-4-carboxylic acid (9) as a white solid. (mp 147°–150° C.)

2-Chloro-cis-(5a,6,7,8,9,9a)-hexahydrodibenzofuran-4-carboxylic acid (3)

The acid 9 (6.5 g, 26.0 mmol) is slurried in (200 mL) of ethanol in a Parr shaker reaction bottle. 5% Palladium on carbon (0.65 g) is added to this and the reaction placed on a Parr shaker. The reaction flask is evacuated and flushed with nitrogen three times then flushed with hydrogen twice before being filled to 35 psi with hydrogen. The reaction is run for 2.5 h. The reaction mixture is filtered through a frit and the catalyst is washed with ethanol (300 mL). The solvent is evaporated under reduced pressure, this material is then dissolved in hexane (15 mL), cooled to 5° C. and filtered to yield 2-chloro-cis-(5a,6,7,8,9,9a)-hexahydrodibenzofuran-4-carboxylic acid (3) as a white solid. (mp 150°–154° C.)

I claim:

1. A process for the preparation of substantially pure 2-chloro-cis-(5a,6,7,8,9,9a-hexahydro)dibenzofuran-4-carboxylic acid by:

(a) heating methyl 5-chloro-3-iodosalicylate with 1,3-cyclohexadiene in the presence of palladium(II-)acetate, tetrabutylammonium chloride and sodium acetate in a polar medium selected from DMF and N,N-dimethylacetamide to obtain 2-chloro-cis-5a,8,9,9a-tetrahydrodibenzofuran-4-methylester;

(b) hydrolyzing 2-chloro-5a,8,9,9a-tetrahydrodibenzofuran-4-methylester with lithium hydroxide monohydrate to obtain 2-chloro-cis-5a,8,9,9a-tetrahydrodibenzofuran-4-carboxylic acid; and (c) reducing 2-chloro-cis-5a,8,9,9a-tetrahydrodibenzofuran-4-carboxylic acid to obtain 2-chloro-cis-(5a,6,7,8,9,9a-hexahydro)dibenzofuran-4-carboxylic acid with 5% palladium on carbon.

* * * * *